United States Patent
Troy et al.

(10) Patent No.: US 11,857,609 B2
(45) Date of Patent: Jan. 2, 2024

(54) OCULAR DELIVERY OF CELL PERMEANT THERAPEUTICS FOR THE TREATMENT OF RETINAL EDEMA

(71) Applicant: THE TRUSTEES OF COLUMBIA UNIVERSITY IN THE CITY OF NEW YORK, New York, NY (US)

(72) Inventors: Carol M. Troy, Hastings-on-Hudson, NY (US); Ying Y. Jean, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/538,924

(22) Filed: Nov. 30, 2021

(65) Prior Publication Data

US 2022/0387565 A1 Dec. 8, 2022

Related U.S. Application Data

(60) Division of application No. 16/243,884, filed on Jan. 9, 2019, now abandoned, which is a continuation of application No. PCT/US2017/041458, filed on Jul. 11, 2017.

(60) Provisional application No. 62/360,721, filed on Jul. 11, 2016.

(51) Int. Cl.
| | |
|---|---|
| *A61K 38/55* | (2006.01) |
| *A61K 9/00* | (2006.01) |
| *A61K 47/64* | (2017.01) |
| *A61P 27/02* | (2006.01) |

(52) U.S. Cl.
CPC ............ *A61K 38/55* (2013.01); *A61K 9/0048* (2013.01); *A61K 47/64* (2017.08); *A61P 27/02* (2018.01)

(58) Field of Classification Search
CPC ...... A61K 38/55; A61K 9/0048; A61K 47/64; A61P 27/02
See application file for complete search history.

(56) References Cited

U.S. PATENT DOCUMENTS

2015/0165061 A1* 6/2015 Troy ...................... A61K 47/64
514/17.7

OTHER PUBLICATIONS

Central Retinal Vein Occlusion, from https://web.archive.org/web/20150321031336/https://preventblindness.org/central-retinal-vein-occlusion/, 2013, pp. 1-2.*
Ottiger et al, Efficient Intraocular Penetration of Topical Anti-TNF-alpha Single-Chain Antibody (ESBA105) to Anterior and Posterior Segment without Penetration Enhancer, Invest Ophthalmol Vis Sci., 2009, 50, pp. 779-786.*
Martinet et al, Macular edema in central retinal vein occlusion: correlation between optical coherence tomography, angiography and visual acuity, Int Ophthalmol, 2012, 32, pp. 369-377.*
Avrutsky et al, Caspase-9 inhibition by Pen1-XBir3 abrogates retinal edema, Abstract submitted for the 2016 ARVO Annual Meeting held on May 1-5, 2016, pp. 1-4.*

* cited by examiner

*Primary Examiner* — Li N Komatsu
(74) *Attorney, Agent, or Firm* — Amster, Rothstein & Ebenstein LLP

(57) ABSTRACT

The present disclosure relates to a method for treating diabetic macular edema (DME) and/or retinal vein occlusion (RVO) comprising administering to the retina of a patient in need thereof an effective amount of a caspase-9 signaling pathway inhibitor. The caspase-9 signaling pathway inhibitor may include a peptide caspase-9 inhibitor and/or may be conjugated to a cell-penetrating peptide. The present disclosure further includes pharmaceutical compositions including a caspase-9 signaling pathway inhibitor. The disclosure further relates to the use of such compositions in a method for treating DME and/or RVO.

19 Claims, 10 Drawing Sheets
(8 of 10 Drawing Sheet(s) Filed in Color)
Specification includes a Sequence Listing.

OCULAR DELIVERY OF CELL PERMEANT THERAPEUTICS FOR THE TREATMENT OF RETINAL EDEMA

PRIORITY CLAIM

The present application is a divisional of U.S. patent application Ser. No. 16/243,884 filed Jan. 9, 2019; which is a continuation of International Application No. PCT/US2017/041458 filed Jul. 11, 2017; which claims priority to U.S. Provisional Patent Application Ser. No. 62/360,721 filed Jul. 11, 2016, the contents of which are incorporated by reference herein in their entirety.

STATEMENT OF GOVERNMENT INTEREST

This invention was made with government support under grant number NS081333 awarded by National Institutes of Health. The government has certain rights in the invention.

SEQUENCE LISTING

The Sequence Listing associated with this application is provided in text format in lieu of a paper copy, and is hereby incorporated by reference into the specification. The name of the text file containing the Sequence Listing is 210271-407D1_SEQ-LISTING_11-30-2021.txt. The text file is 5.57 KB, was created on Nov. 30, 2021, and is being submitted electronically via EFS-Web.

TECHNICAL FIELD

The present disclosure relates to compositions and methods for the inhibition of diabetic macular edema (DME) and/or retinal vein occlusion (RVO).

BACKGROUND

DME is the leading cause of new blindness in the Western world. There are at least 23 million Americans with diabetes mellitus and more than 382 million world-wide; 80% will develop retinopathy and as many as 40% will develop DME. Compounding this problem, only about 50% of patients with diabetes receive proper eye care, and many cases of diabetes are currently not diagnosed. All of this increases the burden of diabetic retinal diseases, including DME and RVO. At present, the only proven pharmacologic option is anti-VEGF therapy which is delivered by intravitreal injection. However, non-compliance is a problem; many patients do not want intraocular injections and miss prescribed doses. Further, it is estimated that as many as 50% of patients with DME will not respond to anti-VEGF therapy. The other treatment is laser photocoagulation, which can reduce vision loss by 50%; the goal is to reduce progression of the disease, however significant improvement of vision is uncommon.

SUMMARY

The present disclosure provides a method for treating DME and/or RVO by administering to the retina of a patient in need thereof an effective amount of a caspase-9 signaling pathway inhibitor.

The present disclosure also provides a pharmaceutical composition including an effective amount of a caspase-9 signaling pathway inhibitor and a pharmaceutically acceptable carrier, wherein the pharmaceutical composition is formulated for administration to a patient via eye drops.

The present disclosure further provides a pharmaceutical composition as described above for use in a method as described above.

The method, pharmaceutical composition, and pharmaceutical composition for use in the method may further include any of the following elements in any combination, unless clearly mutually exclusive: i) the caspase-9 signaling pathway inhibitor may include a peptide caspase-9 inhibitor; ii) the peptide caspase-9 inhibitor may include XBIR3; iii) the caspase-9 signaling pathway inhibitor may be conjugated to a cell-penetrating peptide; iv) the cell-penetrating peptide may be selected from the group consisting of Penetratin1, transportan, pIS1, Tat(48-60), pVEC, MAP, and MTS; v) the caspase-9 signaling pathway inhibitor may include XBIR3 and wherein the XBIR3 is conjugated to Penetratin1; vi) the effective amount may treat DME and/or RVO by decreasing edema in the retina of the patient, as detected by OCT; vii) the effective amount may treat DME and/or RVO by decreasing retinal detachment of the retina of the patient; viii) administering may be via eye drops.

The present specification references various embodiments of the disclosure and provides various examples. These embodiments and examples may also all be used in combination with one another and with any of the above methods, pharmaceutical compositions, or pharmaceutical compositions for use in methods unless they are clearly excluded therefrom.

BRIEF DESCRIPTION OF THE DRAWINGS

This patent or patent application file contains at least one drawing executed in color. Copies of this patent or patent application publication with color drawing(s) will be provided by the Office upon request and payment of the necessary fee.

A more complete understanding of the present embodiments and advantages thereof may be acquired by referring to the following description taken in conjunction with the accompanying drawings, which relate to embodiments of the present disclosure. Certain abbreviations used in these figures and the descriptions thereof are explained in further detail in the remainder of this specification.

DETAILED DESCRIPTION

The present disclosure relates to compositions and method for treating DME and/or RVO in a patient. For example, but not by way of limitation, the present disclosure relates to methods and compositions for inhibiting caspase-9 signaling activity associated with the induction and/or exacerbation of DME and/or RVO in a patient.

As used herein, the term "DME" refers to clinically detectable diabetic macular edema. DME occurs in patients having clinically detectable diabetes mellitus (also referred to herein simply as diabetes), frequently in type 2 diabetes mellitus but also in type 1 diabetes mellitus. Clinical symptoms of DME include retinal edema and diabetic retinopathy with macular edema. DME may be detected using optical coherence tomography (OCT). DME is the major cause of blindness in working age adults (20-70 years old).

As used herein, the term "RVO" refers to clinically detectable retinal vein occlusion. RVO can occur in any patients, but is more common in those also having clinically detectable atherosclerosis, diabetes, hypertension, glaucoma, macular edema, or vitreous hemorrhage. RVO is more common in elderly patients. RVO can cause glaucoma and macular edema, including DME. RVO may be detected using angiography and/or OCT. RVO is the second leading cause of blindness in working age adults.

As used herein, the term "patient" refers to any animal, including any mammal, including, but not limited to, humans, and non-human animals (including, but not limited to, non-human primates, dogs, cats, rodents, horses, cows, pigs, mice, rats, hamsters, rabbits, and the like). In particular, the patient is a human.

As used herein, an "effective amount" is an amount sufficient to cause a beneficial or desired clinical result in a patient. An effective amount can be administered to a patient in one or more doses. It is typically administered to the retina of the patient. In terms of treatment, an effective amount is an amount that is sufficient to ameliorate the impact of and/or inhibit the induction and/or exacerbation of DME and/or RVO in a patient, or otherwise reduce the pathological consequences of the disease(s). The effective amount is generally determined by the physician on a case-by-case basis and is within the skill of one in the art. Several factors may be taken into account when determining an appropriate dosage to achieve an effective amount. These factors include age, the condition being treated, the severity of the condition, prior responses, type of inhibitor used, the caspase-9 signaling pathway member to be inhibited, the cell type expressing the target, and the form and effective concentration of the composition (also referred to herein as a "treatment," "inhibitor," or "conjugate") being administered.

As used herein, "treat," "treating" and similar verbs refer to of ameliorating the impact of and/or inhibiting the induction and/or exacerbation of DME and/or RVO in a patient.

Figure 1:
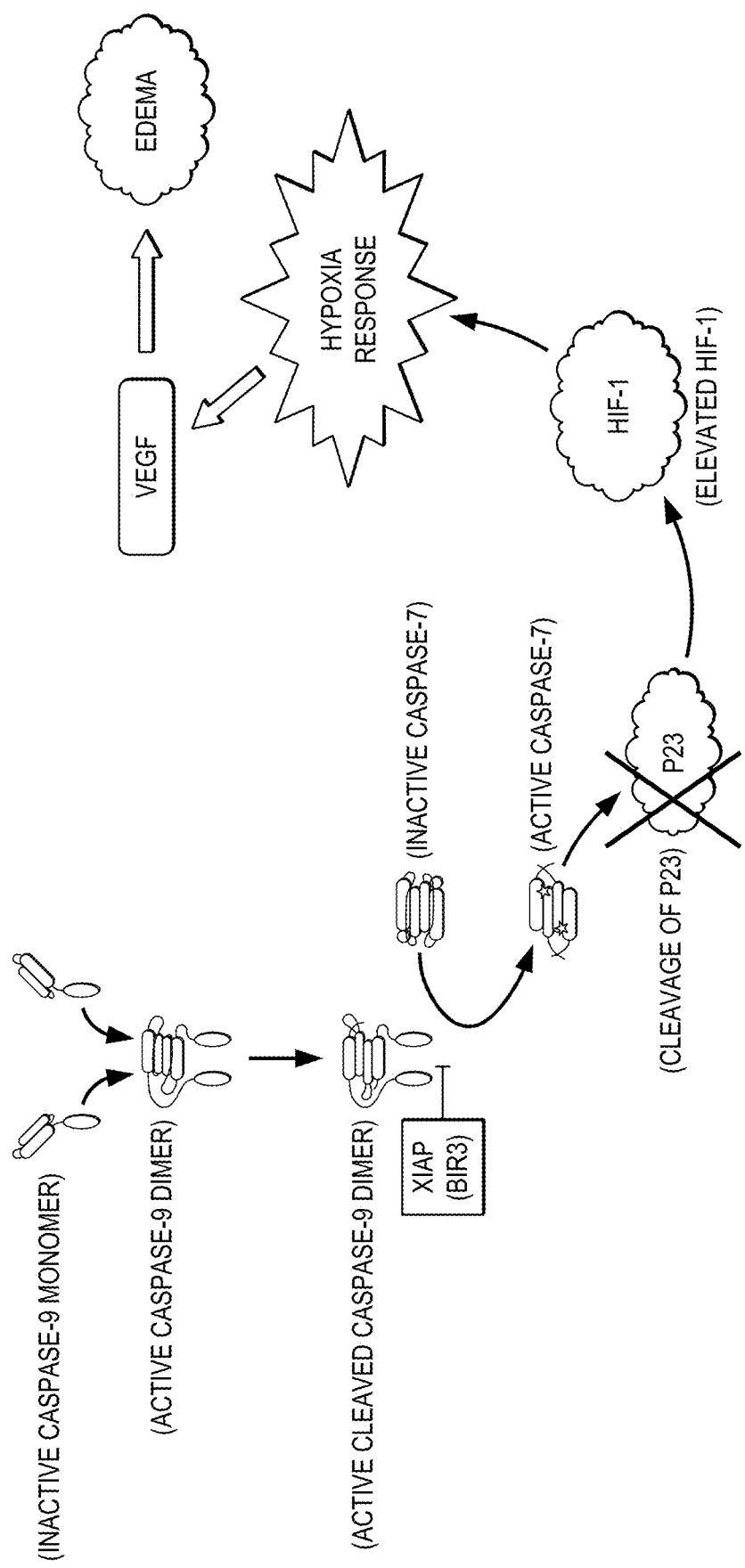
FIG. 1 is a schematic diagram of a caspase-9 mediated signaling pathway that leads to edema unless blocked, for example by Pen1-XBIR3.

Without being limited to a particular mode of action, the caspase-9 signaling pathway as discussed herein may include the pathway shown in FIG. 1. In this pathway, RVO induces activation of caspase-9 in blood vessels which leads to activation of caspase-7. Caspase-7 cleaves the co-chaperone protein p23. p23 is a negative regulator of HIF-1 a, thus cleavage of p23 leads to an increase in HIF-la, the rate-limiting step in the formation of the HIF-1 transcription factor, which increases VEGF levels leading to edema. The caspase-9 signaling pathway inhibitor, shown as Penl-XBIR3 in FIG. 1 as an illustrative example, may act by blocking the action of caspase-9 on caspase-7.

Methods of Inhibiting DME and/or RVO

In certain embodiments, the instant disclosure is directed to methods of or uses of treatments disclosed herein in ameliorating the impact of and/or inhibiting the induction and/or exacerbation of DME and/or RVO in a patient by administering an effective amount of a caspase-9 signaling pathway inhibitor, or conjugate thereof. In certain embodiments, the methods of the present disclosure are directed to the administration of a caspase-9 signaling pathway inhibitor, or conjugate thereof, via eye drops in order to inhibit DME and/or RVO.

The treatment, when used to treat the effects of DME and/or RVO, may be administered as a single dose or multiple doses. For example, but not by way of limitation, where multiple doses are administered, they may be administered at intervals of 6 times per 24 hours or 4 times per 24 hours or 3 times per 24 hours or 2 times per 24 hours or 1 time per 24 hours or 1 time every other day or 1 time every 3 days or 1 time every 4 days or 1 time per week, or 2 times per week, or 3 times per week. In certain embodiments, the initial dose may be greater than subsequent doses or all doses may be the same.

In certain embodiments, the inhibitor used in connection with the methods and uses of the instant disclosure is a Pen l-XBIR3 conjugate as disclosed herein. In certain embodiments, the Penl-XBIR3 conjugate is administered to a patient suffering from DME and/or RVO either as a single dose or in multiple doses. The concentration of the Penl-XBIR3 composition administered is, in certain embodiments: 0.1 µM to 1,000 µM; 1 µM to 500 µM; 10 µM to 100 µM; or 20 µM to 60 µM. In certain embodiments, a specific human equivalent dosage can be calculated from animal studies via body surface area comparisons, as outlined in Reagan-Shaw et al., FASEB J., 22; 659-661 (2007). In certain embodiments, eye size comparisons can be employed to calculate a specific human equivalent dosage.

In certain embodiments, the caspase-9 signaling pathway inhibitor, either alone or in the context of a membrane-permeable conjugate, is administered in conjunction with one or more additional therapeutics. In certain of such embodiments the additional therapeutics include, but are not limited to an anti-VEGF therapeutic and/or a steroidal therapeutic. In certain embodiments the method involves the administration of one or more additional caspase-9 signaling pathway inhibitors either alone or in the context of a membrane-permeable conjugate.

Compositions

Caspase-9 Signaling Pathway Inhibitors

In certain embodiments, the caspase-9 signaling pathway inhibitors of the present disclosure are peptide inhibitors of caspase-9.

In certain embodiments, the caspase-9 signaling pathway inhibitors include, but are not limited to the class of protein inhibitors identified as Inhibitors of ("IAPs"). IAPs generally contain one to three BIR (baculovirus IAP repeats) domains, each consisting of approximately 70 amino acid residues. In addition, certain IAPs also have a RING finger domain, defined by three cysteines, followed by one histidine, followed by four additional cysteines that can coordinate two zinc atoms.

Exemplary mammalian IAPs suitable for use herein, include, but are not limited to c-IAP1 (Accession No. Q13490.2), cIAP2 (Accession No. Q13489.2), and XIAP (Accession No. P98170.2), each of which have three BIRs in the N-terminal portion of the molecule and a RING finger at the C-terminus. NAIP (Accession No. Q13075.3), another suitable mammalian IAP, contains three BIRs without RING, and survivin (Accession No. O15392.2) and BRUCE (Accession No. Q9H8B7), which are two additional suitable IAPs, both of which contain just one BIR.

In certain embodiments the peptide inhibitor of caspase-9 is XBIR3 having the sequence (SEQ ID NO. 11)
MGSSHHHHHHSSGLVPRGSHMSTNTCLPRNPSMADYEARIF

TFGTWIYSVNKEQLARAGFYTDW ALGEGDKVKCFHCGGGL

RPSEDPWEQHARWYPGCRYLLEQRGQEYINNIHL THS.

In certain embodiments the peptide inhibitor of caspase-9 is XBIR3 having the sequence (SEQ ID NO. 12)
MGSSHHHHHHSSGLVPRGSHMSTNTLPRNPSMADYEARIF

TFGTWIYSVNKEQLARAGFYTDW ALGEGDKVKCFHCGGG

LRPSEDPWEQHARWYPGCRYLLEQRGQEYINNIHLTHS.

In certain embodiments the peptide inhibitors of caspase-9 include, but are not limited to EG Z-VEID-FMK ("VEID" disclosed as SEQ ID NO: 1) (WO 2006056487); Z-VAD-FMK, CrmA, and Z-VAD-(2, 6-dichlorobenzoyloxopentanoic acid) (Garcia-Calvo, et al., J. Biol. Chem, 273, 32608-32613 (1998)).

Peptide inhibitors of caspase-9 include those amino acid sequences that retain certain structural and functional features of the identified caspase-9 inhibitor peptides, yet differ from the identified inhibitors' amino acid sequences at one or more positions. Such variants can be prepared by substituting, deleting, or adding amino acid residues from the original sequences via methods known in the art.

In certain embodiments, such substantially similar sequences include sequences that incorporate conservative amino acid substitutions. As used herein, a "conservative amino acid substitution" is intended to include a substitution in which the amino acid residue is replaced with an amino acid residue having a similar side chain. Families of amino acid residues having similar side chains have been defined in the art, including: basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); P-branched side chains (e.g., threonine, valine, isoleucine); and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptides can be prepared by standard techniques, such as automated chemical synthesis.

In certain embodiments, a peptide inhibitor of caspase-9 of the present disclosure is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of the original peptide inhibitor of caspase-9, such as an IAP, and is capable of caspase-9 inhibition. As used herein, the percent homology between two amino acid sequences may be determined using standard software such as BLAST or FASTA The effect of the amino acid substitutions on the ability of the synthesized peptide inhibitor of caspase-9 to inhibit caspase-9 can be tested using the methods disclosed in Examples section, below.

Inhibitor-Cell Penetrating Peptide Conjugates

In certain embodiments of the present disclosure, the caspase-9 signaling pathway inhibitor is conjugated to a cell penetrating peptide to form an inhibitor-cell penetrating peptide conjugate.

As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. In certain embodiments, the cell-penetrating peptide used in the membrane-permeable complex of the present disclosure preferably comprises at least one non-functional cysteine residue, which is either free or derivatized to form a disulfide link with the caspase-9 signaling pathway inhibitor, which has been modified for such linkage. Representative amino acid motifs conferring such properties are listed in U.S. Pat. No. 6,348,185, the contents of which are expressly incorporated herein by reference. The cell-penetrating peptides of the present disclosure may include, but are not limited to, Penetratinl, transportan, pisl, TAT(48-60), pVEC, MTS, and MAP.

The cell-penetrating peptides of the present disclosure include those sequences that retain certain structural and functional features of the identified cell-penetrating peptides, yet differ from the identified peptides' amino acid sequences at one or more positions. Such polypeptide variants can be prepared by substituting, deleting, or adding amino acid residues from the original sequences via methods known in the art.

In certain embodiments, such substantially similar sequences include sequences that incorporate conservative amino acid substitutions, as described above in connection with peptide caspase-9 inhibitors. In certain embodiments, a cell-penetrating peptide of the present disclosure is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of the identified peptide and is capable of mediating cell penetration. The effect of the amino acid substitutions on the ability of the synthesized peptide to mediate cell penetration can be tested using the methods in Examples section, below.

In certain embodiments of the present disclosure, the cell-penetrating peptide of the membrane-permeable complex is Penetratin1, comprising the peptide sequence C(NPys)-RQIKIWFQNRRMKWKK (SEQ ID NO: 2), or a conservative variant thereof. As used herein, a "conservative variant" is a peptide having one or more amino acid substitutions, wherein the substitutions do not adversely affect the shape—or, therefore, the biological activity (i.e., transport activity) or membrane toxicity—of the cell-penetrating peptide.

Penetratin1 is a 16-amino-acid polypeptide derived from the third alpha-helix of the homeodomain of Drosophila antennapedia. Its structure and function have been well studied and characterized: Derossi et al., Trends Cell Biol., 8(2):84-87, 1998; Dunican et al., Biopolymers, 60(1):45-60, 2001; Hallbrink et al., Biochim. Biophys. Acta, 1515(2): 101-09, 2001; Bolton et al., Eur. J. Neurosci., 12(8):2847-55, 2000; Kilk et al., Bioconjug. Chem, 12(6):911-16, 2001; Bellet-Amalric et al., Biochim Biophys. Acta, 1467(1):131-43, 2000; Fischer et al., J. Pept. Res., 55(2):163-72, 2000; Thoren et al., FEBS Lett., 482(3):265-68, 2000.

It has been shown that Penetratin1 efficiently carries avidin, a 63-kDa protein, into human Bowes melanoma cells (Kilk et al., Bioconjug. Chem, 12(6):911-16, 2001). Additionally, it has been shown that the transportation of Penetratin1 and its cargo is non-endocytotic and energy-independent, and does not depend upon receptor molecules or transporter molecules. Furthermore, it is known that Penetratin1 is able to cross a pure lipid bilayer (Thoren et al., FEBS Lett., 482(3):265-68, 2000). This feature enables Penetratin1 to transport its cargo, free from the limitation of cell-surface-receptor/-transporter availability. The delivery vector previously has been shown to enter all cell types (Derossi et al., Trends Cell Biol., 8(2):84-87, 1998), and effectively to deliver peptides (Troy et al., Proc. Natl. Acad. Sci. USA, 93:5635-40, 1996) or antisense oligonucleotides (Troy et al., J. Neurosci., 16:253-61, 1996; Troy et al., J. Neurosci., 17:1911-18, 1997).

Other non-limiting embodiments of the present disclosure involve the use of the following exemplary cell permeant molecules: RL16 (H-RRLRRLLRRLLRRLRR-OH) (SEQ ID NO: 3), a sequence derived from Penetratin1 with slightly different physical properties (Biochim Biophys Acta. 2008 July-;1 780(7-8):948-59); and RVG-RRRRRRRRR (SEQ ID NO: 4), a rabies virus sequence which targets neurons see P. Kumar, H. Wu, J. L. McBride, K. E. Jung, M. H. Kim, B. L. Davidson, S. K. Lee, P. Shankar and N. Manjunath, Transvascular delivery of small interfering RNA to the central nervous system, Nature 448 (2007), pp. 39-43.

In certain alternative non-limiting embodiments of the present disclosure, the cell-penetrating peptide of the membrane-permeable complex is a cell-penetrating peptide selected from the group consisting of: transportan, pIS1, Tat(48-60), pVEC, MAP, and MTS. Transportan is a 27-amino-acid long peptide containing 12 functional amino acids from the amino terminus of the neuropeptide galanin, and the 14-residue sequence of mastoparan in the carboxyl terminus, connected by a lysine (Pooga et al., FASEB J., 12(1):67-77, 1998). It includes the amino acid sequence GWTLNSAGYLLGKINLKALAALAKKIL (SEQ ID NO: 5), or a conservative variant thereof.

pIs1 is derived from the third helix of the homeodomain of the rat insulin 1 gene enhancer protein (Magzoub et al., Biochim Biophys. Acta, 1512(1):77-89, 2001; Kilk et al., Bioconjug. Chem, 12(6):911-16, 2001). pis1 includes the amino acid sequence PVIRVW FQNKRCKDKK (SEQ ID NO: 6), or a conservative variant thereof.

Tat is a transcription activating factor, of 86-102 amino acids, that allows translocation across the plasma membrane of an HIV-infected cell, to transactivate the viral genome (Hallbrink et al., Biochem Biophys. Acta., 1515(2):101-09, 2001; Suzuki et al., J. Biol. Chem, 277(4):2437-43, 2002; Futaki et al., J. Biol. Chem, 276(8):5836-40, 2001). A small Tat fragment, extending from residues 48-60, has been determined to be responsible for nuclear import (Vives et al., J. Biol. Chem, 272(25):16010-017, 1997); it includes the amino acid sequence GRKKRRQRRRPPQ (SEQ ID NO: 7), or a conservative variant thereof.

pVEC is an 18-amino-acid-long peptide derived from the murine sequence of the cell-adhesion molecule, vascular endothelial cadherin, extending from amino acid 615-632 (Elmquist et al., Exp. Cell Res., 269(2):237-44, 2001). pVEC includes the amino acid sequence LLIILRR-RIRKQAHAH (SEQ ID NO: 8), or a conservative variant thereof.

MTSs, or membrane translocating sequences, are those portions of certain peptides which are recognized by the acceptor proteins that are responsible for directing nascent translation products into the appropriate cellular organelles for further processing (Lindgren et al., Trends in Pharmacological Sciences, 21(3):99-103, 2000; Brodsky, J. L., Int. Rev. Cyt., 178:277-328, 1998; Zhao et al., J. Immunol. Methods, 254(1-2):137-45, 2001). An MTS of particular relevance is MPS peptide, a chimera of the hydrophobic terminal domain of the viral gp41 protein and the nuclear localization signal from simian virus 40 large antigen; it represents one combination of a nuclear localization signal and a membrane translocation sequence that is internalized independent of temperature, and functions as a carrier for oligonucleotides (Lindgren et al., Trends in Pharmacological Sciences, 21(3): 99-103, 2000; Morris et al., Nucleic Acids Res., 25:2730-36, 1997). MPS includes the amino acid sequence GALFLGWLGAAGSTMGAWSQPKKKRKV (SEQ ID NO: 9), or a conservative variant thereof.

Model amphipathic peptides, or MAPs, form a group of peptides that have, as their essential features, helical amphipaticity and a length of at least four complete helical turns (Scheller et al., J. Peptide Science, 5(4):185-94, 1999; Hallbrink et al., Biochim. Biophys. Acta., 1515(2):101-09, 2001). An exemplary MAP comprises the amino acid sequence KLALKLALKALKAALKLA (SEQ ID NO: 10)-amide, or a conservative variant thereof.

In certain embodiments, the cell-penetrating peptides and the caspase-9 signaling pathway inhibitors described above are covalently bound to form conjugates. In certain embodiments the cell-penetrating peptide is operably linked to a peptide caspase-9 inhibitor via recombinant DNA technology. For example, in embodiments where the caspase-9 signaling pathway inhibitor is a peptide caspase-9 inhibitor, a nucleic acid sequence encoding that peptide caspase-9 inhibitor can be introduced either upstream (for linkage to the amino terminus of the cell-penetrating peptide) or downstream (for linkage to the carboxy terminus of the cell-penetrating peptide), or both, of a nucleic acid sequence encoding the peptide caspase-9 inhibitor of interest. Such fusion sequences including both the peptide caspase-9 inhibitor encoding nucleic acid sequence and the cell-penetrating peptide encoding nucleic acid sequence can be expressed using techniques well known in the art.

In certain embodiments the caspase-9 signaling pathway inhibitor can be operably linked to the cell-penetrating peptide via a non-covalent linkage. In certain embodiments such non-covalent linkage is mediated by ionic interactions, hydrophobic interactions, hydrogen bonds, or van der Waals forces.

In certain embodiments the caspase-9 signaling pathway inhibitor is operably linked to the cell penetrating peptide via a chemical linker. Examples of such linkages typically incorporate 1-30 nonhydrogen atoms selected from the group consisting of C, N, O, S and P. Exemplary linkers include, but are not limited to, a substituted alkyl or a substituted cycloalkyl. Alternately, the heterologous moiety may be directly attached (where the linker is a single bond) to the amino or carboxy terminus of the cell-penetrating peptide. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In certain embodiments, the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. In certain embodiments, the linker is a combination of single carbon-carbon bonds and carboxamide, sulfonamide or thioether bonds.

A general strategy for conjugation involves preparing the cell-penetrating peptide and the caspase-9 signaling pathway inhibitor components separately, wherein each is modified or derivatized with appropriate reactive groups to allow for linkage between the two. The modified caspase-9 signaling pathway inhibitor is then incubated together with a cell-penetrating peptide that is prepared for linkage, for a sufficient time (and under such appropriate conditions of temperature, pH, molar ratio, etc.) as to generate a covalent bond between the cell-penetrating peptide and the caspase-9 signaling pathway inhibitor molecule.

Numerous methods and strategies of conjugation will be readily apparent to one of ordinary skill in the art, as will the conditions required for efficient conjugation. By way of example only, one such strategy for conjugation is described below, although other techniques, such as the production of fusion proteins or the use of chemical linkers is within the scope of the present disclosure.

In certain embodiments, when generating a disulfide bond between the caspase-9 signaling pathway inhibitor molecule and the cell-penetrating peptide of the present disclosure, the caspase-9 signaling pathway inhibitor molecule can be modified to contain a thiol group, and a nitropyridyl leaving group can be manufactured on a cysteine residue of the cell-penetrating peptide. Any suitable bond (e.g., thioester bonds, thioether bonds, carbamate bonds, etc.) can be created according to methods generally and well known in the art. Both the derivatized or modified cell-penetrating peptide, and the modified caspase-9 signaling pathway inhibitor are reconstituted in RNase/DNase sterile water, and then added to each other amounts appropriate for conjugation (e.g., equimolar amounts). The conjugation mixture is then incubated for 60 min at 37° C., and then stored at 4° C. Linkage can be checked by running the vector-linked caspase-9 signaling pathway inhibitor molecule, and an aliquot that has been reduced with DTT, on a 15% non-denaturing PAGE. Caspase-9 signaling pathway inhibitor molecules can then be visualized with the appropriate stain.

In certain embodiments, the present disclosure is directed to a Penetratin1-XBIR3 (Pen1-XBIR3) conjugate. In certain of such embodiments, the sequence of the Pen-1-XBIR3 is: C(NPys)-RQIKIWFQNRRMKWKK-s-s-MGSSHHHHHHSSGLVPRGSHMSTNTCLPRNPSMAD-YEARIFTFGTWIYSVNK EQLARAGFYTDW ALGEGDKVKCFHCGGGLRPSEDPWEQHARWYPGC-RYLL EQRGQEYINNIHL THS (SEQ ID NO 2 and 11, respectively, linked by a disulfide bond). In other of such embodiments, the sequence of the Pen1-XBIR3 is: C(NPys)-RQIKIWFQNRRMKWKK-s-s-MGSSHHHHHHSSGLVPRGSHMSTNTLPRNPSMAD-YEARIFTFGTWIYSVNKE QLARAGFYTDW ALGEGDKVKCFHCGGGLRPSEDPWEQHARWYPGC-RYLLE QRGQEYINNIHLTHS (SEQ ID NO 2 and 12, respectively, linked by a disulfide bond).

Pharmaceutical Compositions

In certain embodiments, the caspase-9 signaling pathway inhibitors or conjugates of the present disclosure are formulated for retinal administration. For administration via eye drops, a solution or suspension containing the caspase-9 signaling pathway inhibitor or conjugate can be formulated for direct application to the retina by conventional means, for example with a dropper, pipette or spray. In certain embodiments, the caspase-9 signaling pathway inhibitor or conjugate of the present disclosure is formulated in isotonic saline. In certain embodiments, the caspase-9 signaling pathway inhibitor or conjugate of the present disclosure is formulated in isotonic saline at or about pH 7.4.

To facilitate delivery to a cell, tissue, or subject, the caspase-9 signaling pathway inhibitor, or conjugate thereof, of the present disclosure may, in various compositions, be formulated with a pharmaceutically-acceptable carrier, excipient, or diluent. The term "pharmaceutically-acceptable", as used herein, means that the carrier, excipient, or diluent of choice does not adversely affect either the biological activity of the caspase-9 signaling pathway inhibitor or conjugate or the biological activity of the recipient of the composition. Suitable pharmaceutical carriers, excipients, and/or diluents for use in the present disclosure include, but are not limited to, lactose, sucrose, starch powder, talc powder, cellulose esters of alkonoic acids, magnesium stearate, magnesium oxide, crystalline cellulose, methyl cellulose, carboxymethyl cellulose, gelatin, glycerin, sodium alginate, gum arabic, acacia gum, sodium and calcium salts of phosphoric and sulfuric acids, polyvinylpyrrolidone and/or polyvinyl alcohol, saline, and water. Specific formulations of compounds for therapeutic treatment are discussed in Hoover, J. E., Remington's Pharmaceutical Sciences (Easton, Pa.: Mack Publishing Co., 1975) and Liberman and Lachman, eds. Pharmaceutical Dosage Forms (New York, N.Y.: Marcel Decker Publishers, 1980).

In accordance with the methods of the present disclosure, the quantity of the caspase-9 signaling pathway inhibitor or conjugate thereof that is administered to a cell, tissue, or subject should be an effective amount.

EXAMPLES

Example 1: Eyedrops Deliver Pen1-XBIR3 to Mouse and Rabbit Retinas

Figure 2:
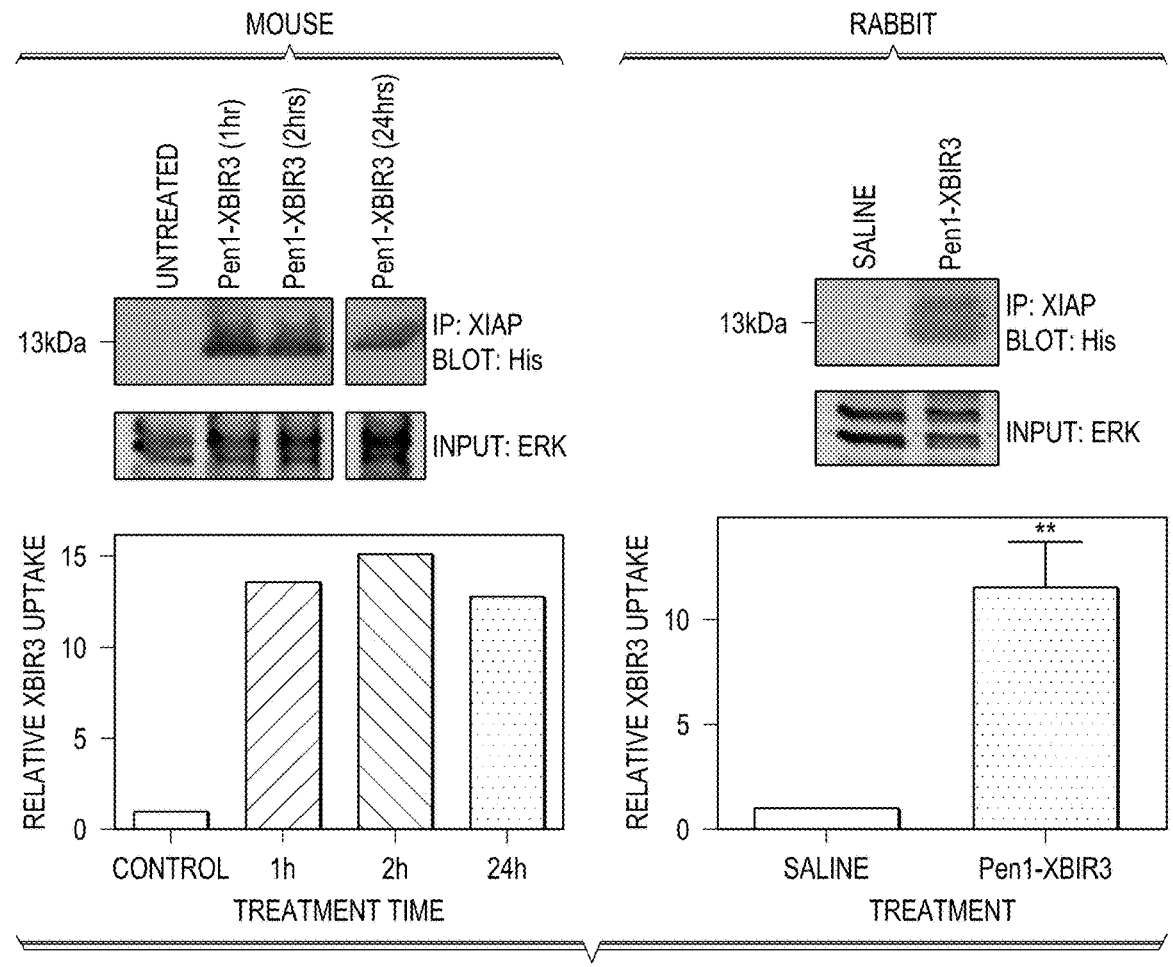
FIG. 2 is a set of blots and corresponding bar graphs presenting results for uptake of Pen1-XBIR3 eyedrops by the retina in mice and rabbits.
Figure 3:
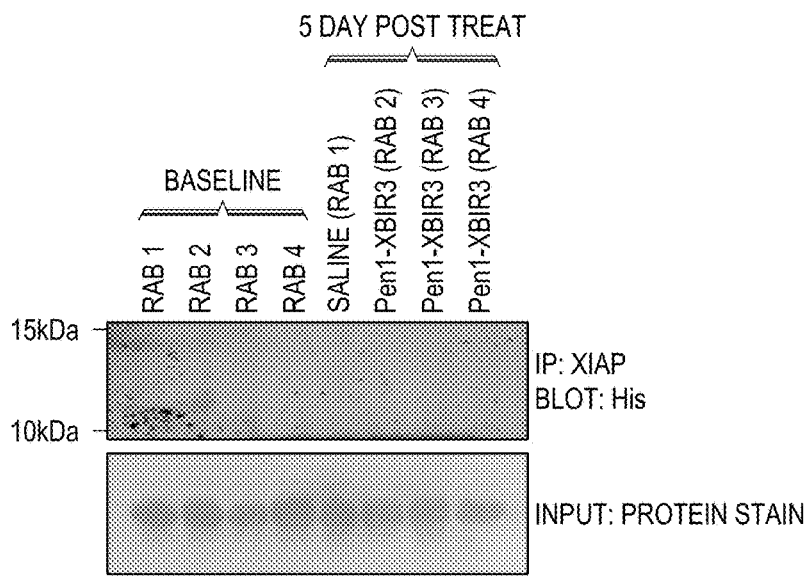
FIG. 3 is a set of blots presenting results for presence of Pen1-XBIR3 in the plasma of rabbits after eyedrop treatment.

The ability of eyedrops to deliver Pen1-XBIR3 in mice and rats was tested. Results are presented in FIG. 2 and FIG. 3.

In mice, Pen1-XBIR3 (10 µg) eyedrops were applied, then the animals were sacrificed at the indicated times. In rabbits, 200 μg Penl-XBIR3 eyedrops or a saline vehicle were administered BID for 4.5 days. The final dose given 5 h prior to harvest of retinas. Plasma from rabbits obtained at baseline and harvest.

Retinal lysates were immunoprecipitated with XIAP, followed by western blotting for anti-His. XBIR3 contains a His tag, so uptake of XBIR3 is detectable using anti-His. Blots for the mouse and rabbit samples, along with graphs quantifying the results, are presented in FIG. 2. XBIT3 uptake was observed in both mouse and rabbit samples. Uptake in the mouse samples was detected by 1 h and maintained through 24 h. In rabbit there was significant XBIR3 in retina at 5d.

Baseline and post-treatment plasma from rabbits was analyzed by immunoprecipitation with XIAP followed by western blot with anti-His. A Ponceau protein stain was used to show input protein amounts. XBIR3 was not detected in rabbit plasma (FIG. 3), indicating that it remains localized in the eye.

Example 2: Mouse Model of RVO

In the following experiments, a mouse model of RVO, which induces reproducible retinal edema was used. RVO is the model that was used for testing anti-VEGF therapies for DME. Brown et al., Ophthalmology 117, 1124-1133 el 121 (2010); and Campochiaro et al., Ophthalmology 117, 1102-1112 e1101 (2010). I n this model, Rose Bengal, a photo-activatable dye, is injected into the tail veins of adult C57B16 mice and photoactivated by laser of retinal veins around the optic nerve head. A clot is formed and edema or increased retinal thickness develops rapidly. Inflammation, also seen in diabetes, also develops.

Fluorescein leakage and maximal retinal edema, measured by fluorescein angiography and optical coherence tomography (OCT), respectively, using the Phoenix Micron IV, is observed 24 h after RVO. Retinal edema is maintained over the first 3 days RVO. By day 4 the edema decreases and the retina subsequently thins out. In addition to edema formation there is evidence of cell death in the photoreceptor cell layer by day 2 after RVO.

In this example, mice were anesthetized with intra-peritoneal (IP) injection of ketamine and xylazine. One drop of 0.5% alcaine was added to the eye as topical anesthetic. The retina was imaged with the Phoenix Micron IV to choose veins for laser ablation using the Phoenix Micron IV image guided laser. One to four veins around the optic nerve head were ablated by delivering a laser pulse (power 50 mW, spot size 50 μm, duration 3 seconds) to each vein.

Example 3: Target Activation and Engagement

Penl-XBIR3 eyedrops were delivered immediately after RVO and at 24 h. At 48 h, the eyes were imaged via OCT.

Figure 4:
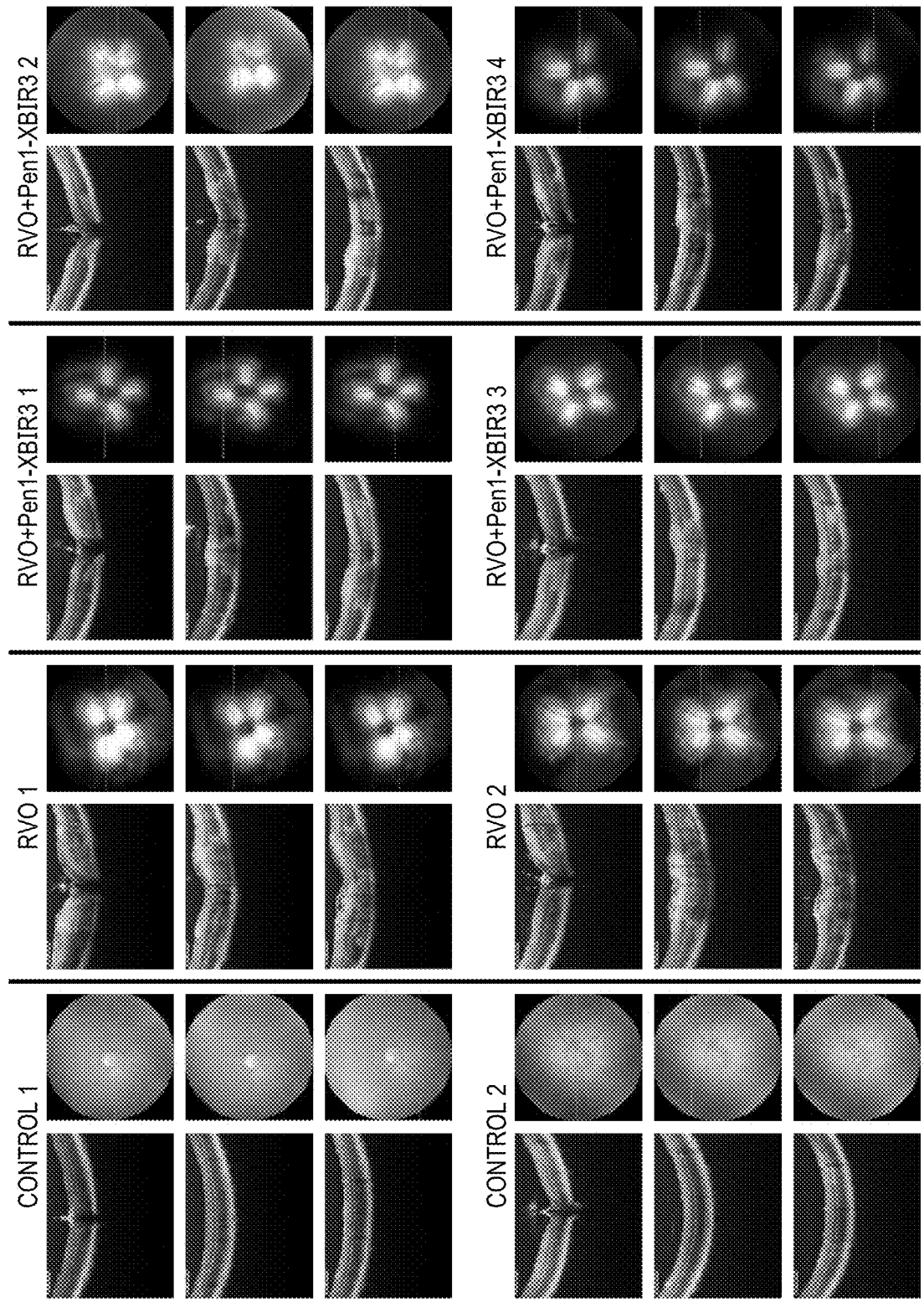
FIG. 4 is a series of brightfield and OCT images showing the effects of RVO or RVO and Pen1-XBIR3 on retinal edema.

FIG. 4 presents images from individual animals (2 control, 2 RVO, 4 RVO+Penl-XBIR3). For each animal there are three sets of OCT and brightfield images. The brightfield image has a horizontal line showing the level of the OCT.

Figure 5:
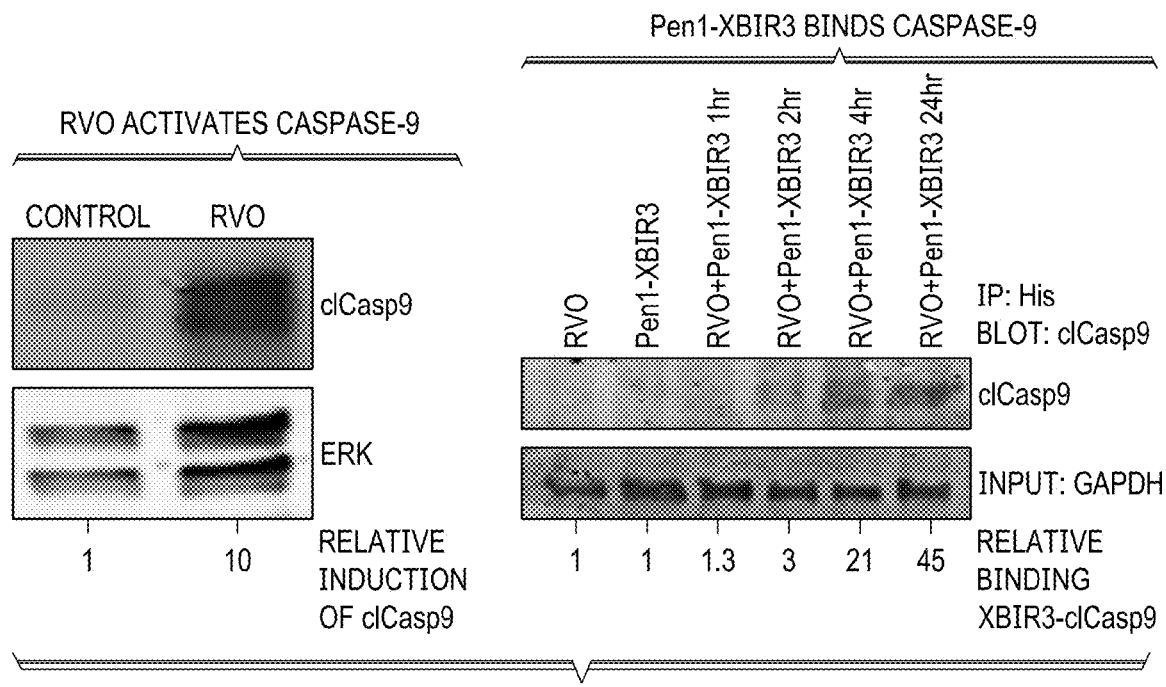
FIG. 5 is a set of blots depicting results of assays for RVO activation of caspase-9 (left) and Pen1-XBIR3 binding of caspase-9 (right).

Four hours after RVO, mouse retinas were harvested for western blot to detect activated caspase-9 (c1Casp9) (FIG. 5, left panel). The blot showed a 10-fold induction of c1Casp9.

To show target engagement, after RVO, mice were given Penl-XBIR3 and retinas were harvested and immunoprecipitated with anti-His followed by western blot for clCasp9 (FIG. 5, right panel). There was a 21-fold increase in binding of XBIR3 and clCasp9 by 4 h and a 45-fold increase by 24 h.

Example 4: Penl-XBIR3 Provided Significant Protection in RVO

Figure 6:
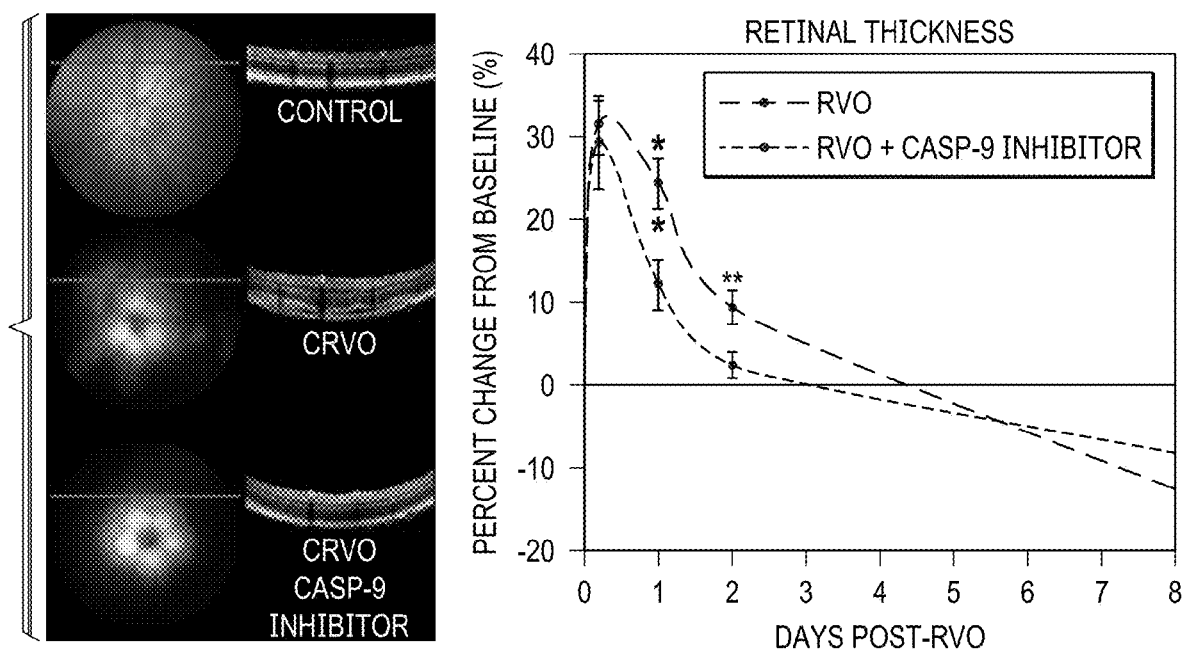
FIG. 6 is a series of brightfield and OCT images and a graph showing effects of RVO or RVO and Pen1-XBIR3 (caspase-9 inhibitor) on retina edema.

The efficacy of Penl-XBIR3 eyedrops in RVO was evaluated. Penl-XBIR3 eyedrops were given immediately after RVO and at 24 h. At 48 h OCT images showed significant protection against RVO (FIG. 6) with less increase in retinal thickness and abrogation of retinal detachment (**$P<0.01$).

Figure 7:
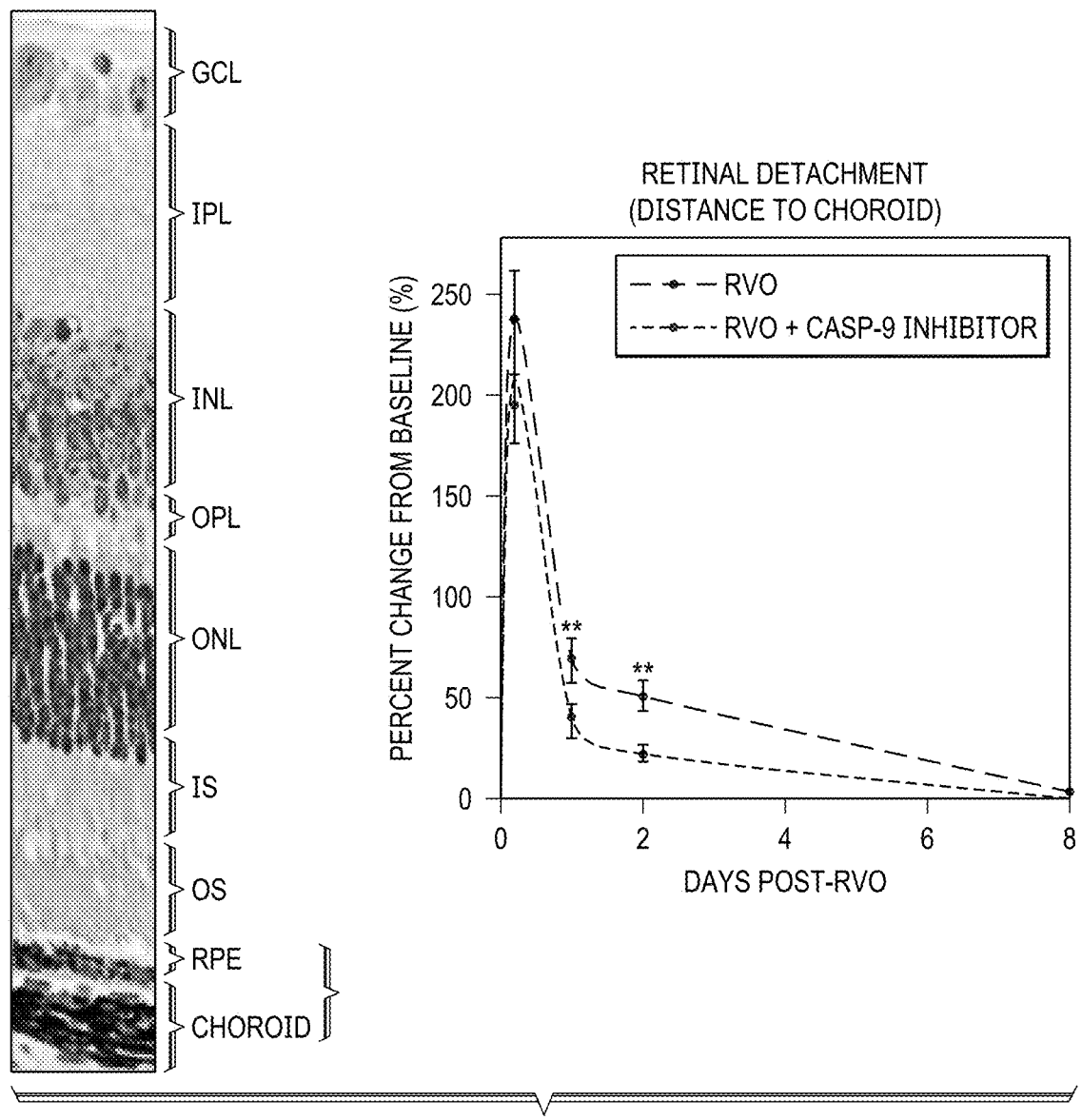
FIG. 7 is a representative OCT image and a graph showing effects of RVO or RVO and Pen1-XBIR3 (caspase-9 inhibitor) on retinal detachment.
Figure 8:
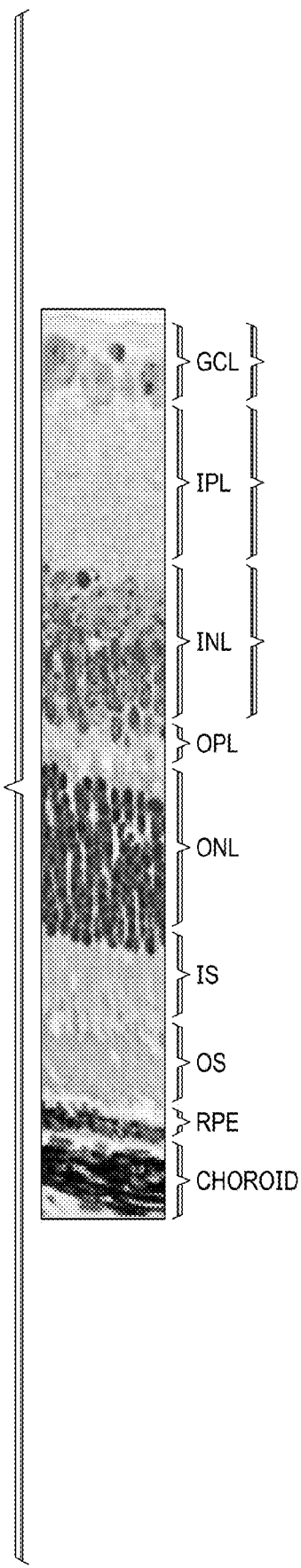
FIG. 8 is a representative OCT image and a series of graphs showing the effects of RVO or RVO and Pen1-XBIR3 (caspase-9 inhibitor) on internal retinal layers.
Figure 8:
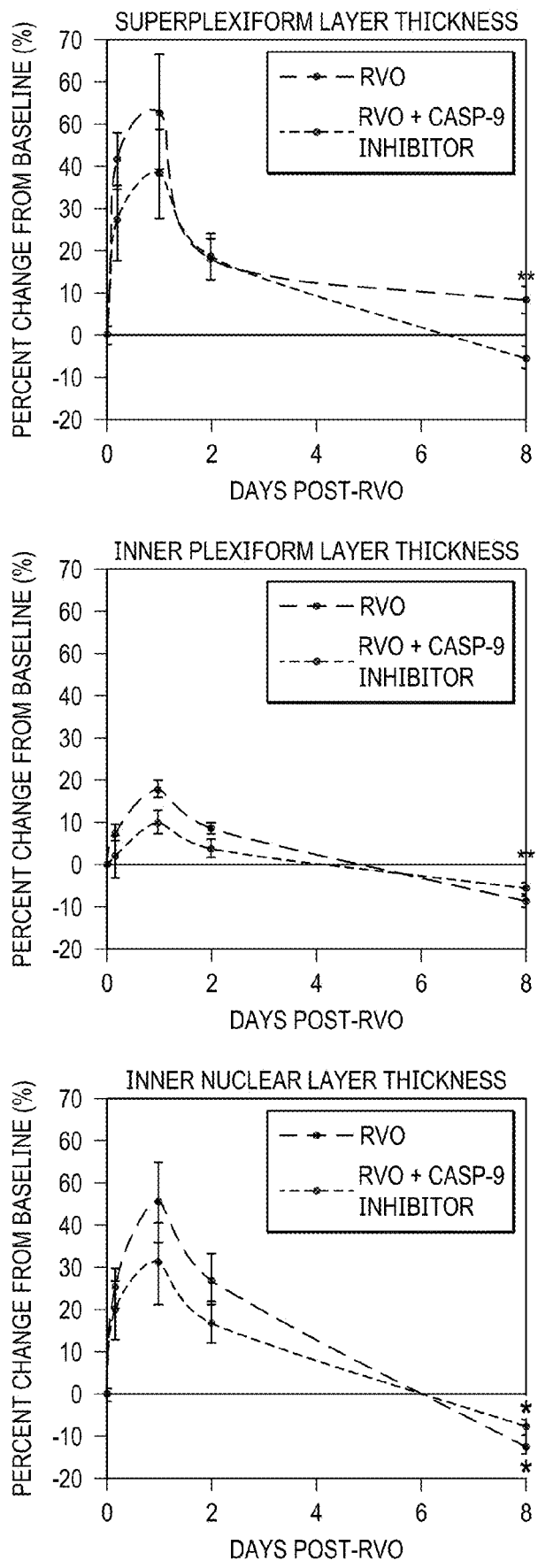
Figure 9:
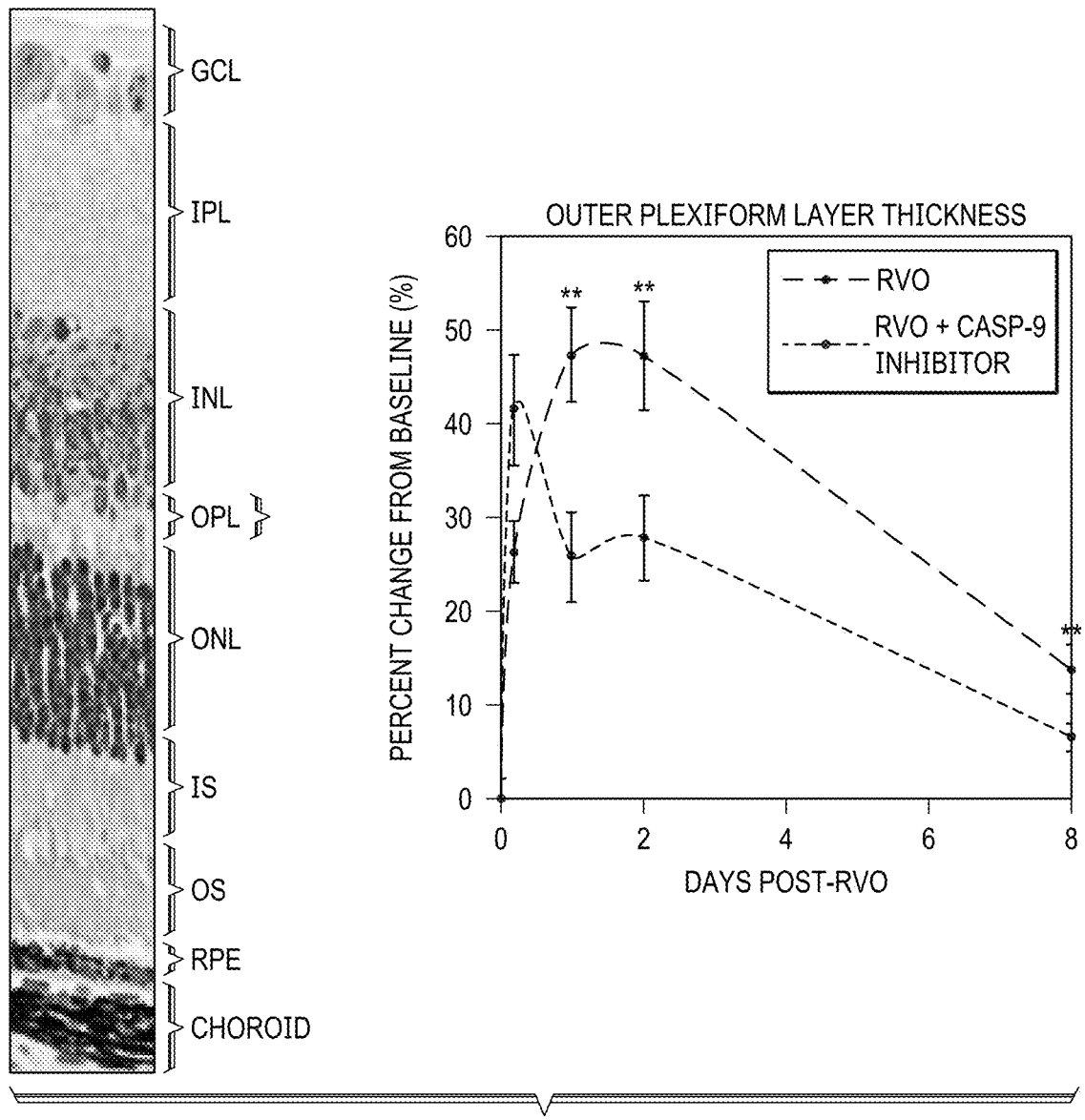
FIG. 9 is a representative OCT image and a graph showing the effects of RVO or RVO and Penl-XBIR3 (caspase-9 inhibitor) on the retinal outer plexiform layer.
Figure 10:
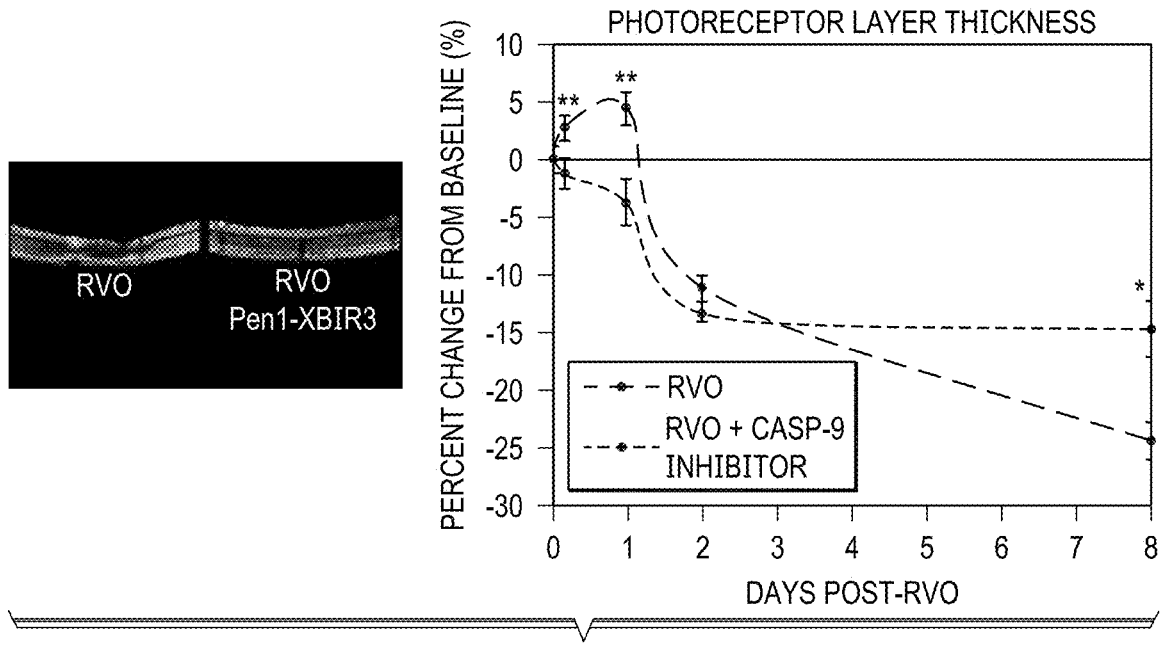
FIG. 10 is a set of representative OCT images and a graph showing the effects of RVO or RVO and Penl-XBIR3 (caspase-9 inhibitor) on the retinal photoreceptor layer.

Individual retinal layers were also examined, as they are not affected equally by RVO. Retinal layers include the ganglion cell layer (GCL), the inner plexiform layer (IPL), the inner nuclear layer (INL), the outer plexiform layer (OPL), the outer nuclear layer (ONL), the inner segments (IS), the outer segments (OS), and the retinal pigment epithelium (RPE), which is located next to the choroid. Penl-XBIR3 decreased retinal detachment (FIG. 7, $P<0.01$), protected the inner retinal layers (FIG. 8, $P<0.01$), decreased swelling of the outer retina layers, such as the outer plexiform layer (FIG. 9, $P<0.01$) and protected the photoreceptors (FIG. 10**, *$P<0.05$, **$P<0.01$).

Example 5: Penl-XBIR3 Blocked Cell Death after RVO

Figure 11:
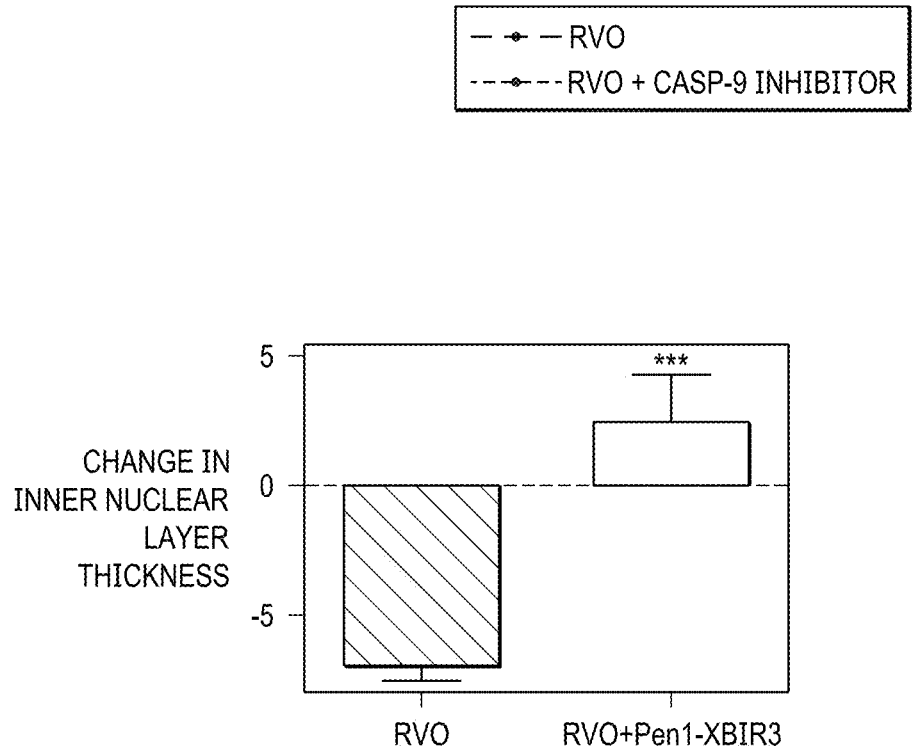
FIG. 11 is a graph of the effects of RVO or RVO and Penl-XBIR3 on retinal inner nuclear layer thickness.

TUNEL staining is a marker of cell death. RVO induces TUNEL staining by 24 h in the INL. Retinas were harvested at 48 h from mice treated with Penl-XBIR3 or untreated mice, then processed for immunohistochemistry. Analysis of samples showed that TUNEL positive cells were decreased by Penl-XBIR3 eyedrops and that the eyedrops maintained INL thickness (FIG. 11).

Example 6: Penl-XBIR3 Provided Functional Protection in RVO

Figure 12:
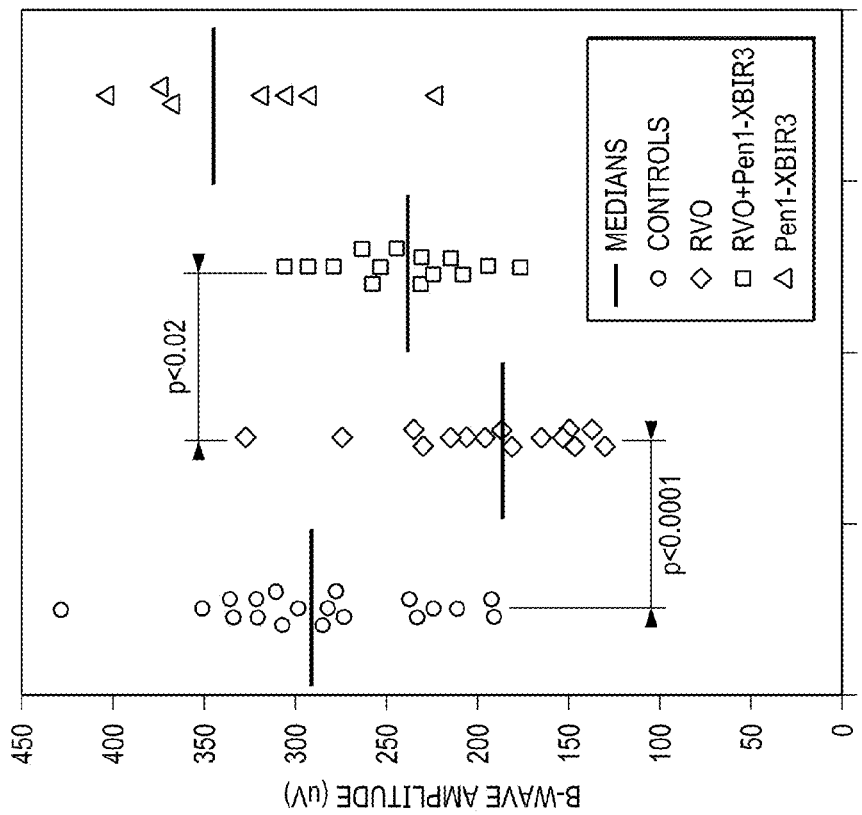
FIG. 12 is a graph of the effects of RVO, Penl-XBIR3, or RVO and Penl-XBIR3 on B-wave amplitude, which relates to retinal function.

RVO induces a decrease in A and B waves on an electroretinogram (ERG). Treatment with Penl-XBIR3 immediately after RVO and at 24 h provided ERG improvement (scoptic focal ERG, spot size 1500 μm, flash intensity -2.3 log $cd/m^2$) up to 7d post-RVO (FIG. 12).

Example 7: Penl-XBIR3 Prevented an Increase in Cleaved Caspase-7 after RVO

Figure 13:
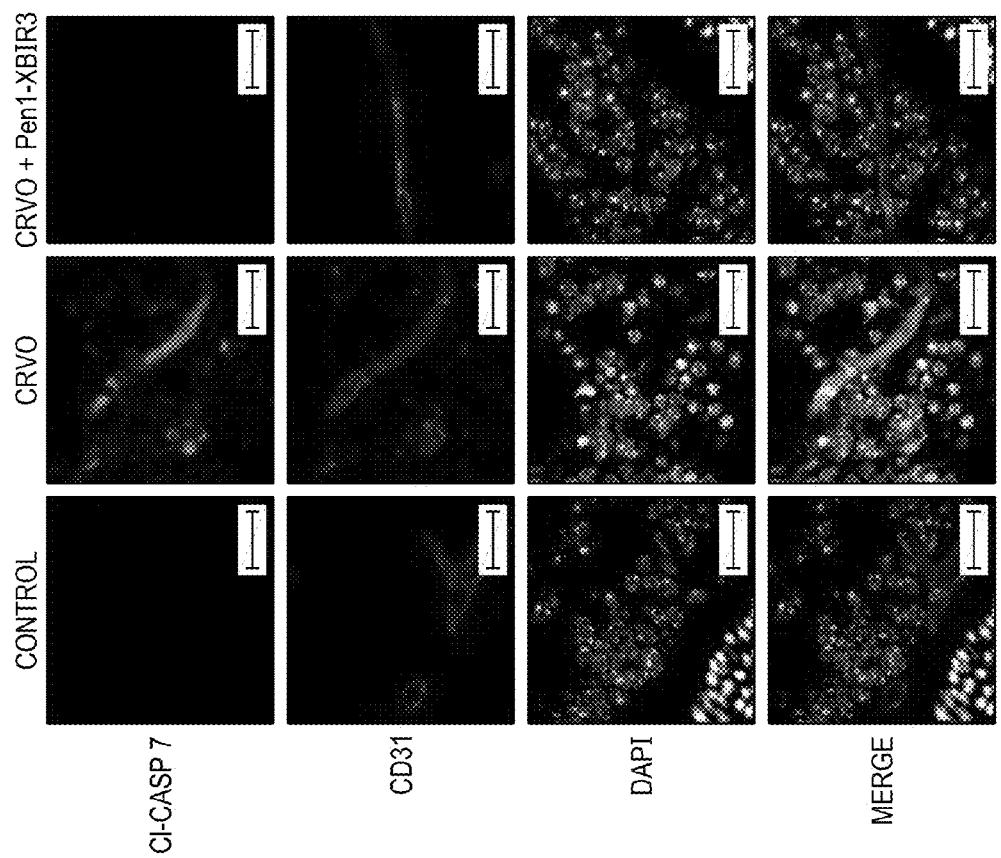
FIG. 13 is a series of photomicrographs stained to allow detection of cleaved caspase-7 in retinal blood vessels to show the effects of RVO or RVO and Penl-XBIR3. The scale bar is 20 µm.

RVO induces activation of caspase-7, a target of active caspase-9, in blood vessels. Penl-XBIR3 prevents this increase at 24 h as shown by a comparison of retinal section obtained 24 h post-RVO and stained as indicated (FIG. 13.)

Example 8: Penl-XBIR3 Prevented Induction of VEGF and HIF-1a by RVO

RVO leads to induction of vascular endothelial growth factor (VEGF) and Hypoxia-inducible factor I-alpha (HIF-1a) within 4 h of induction of RVO.

Figure 14:
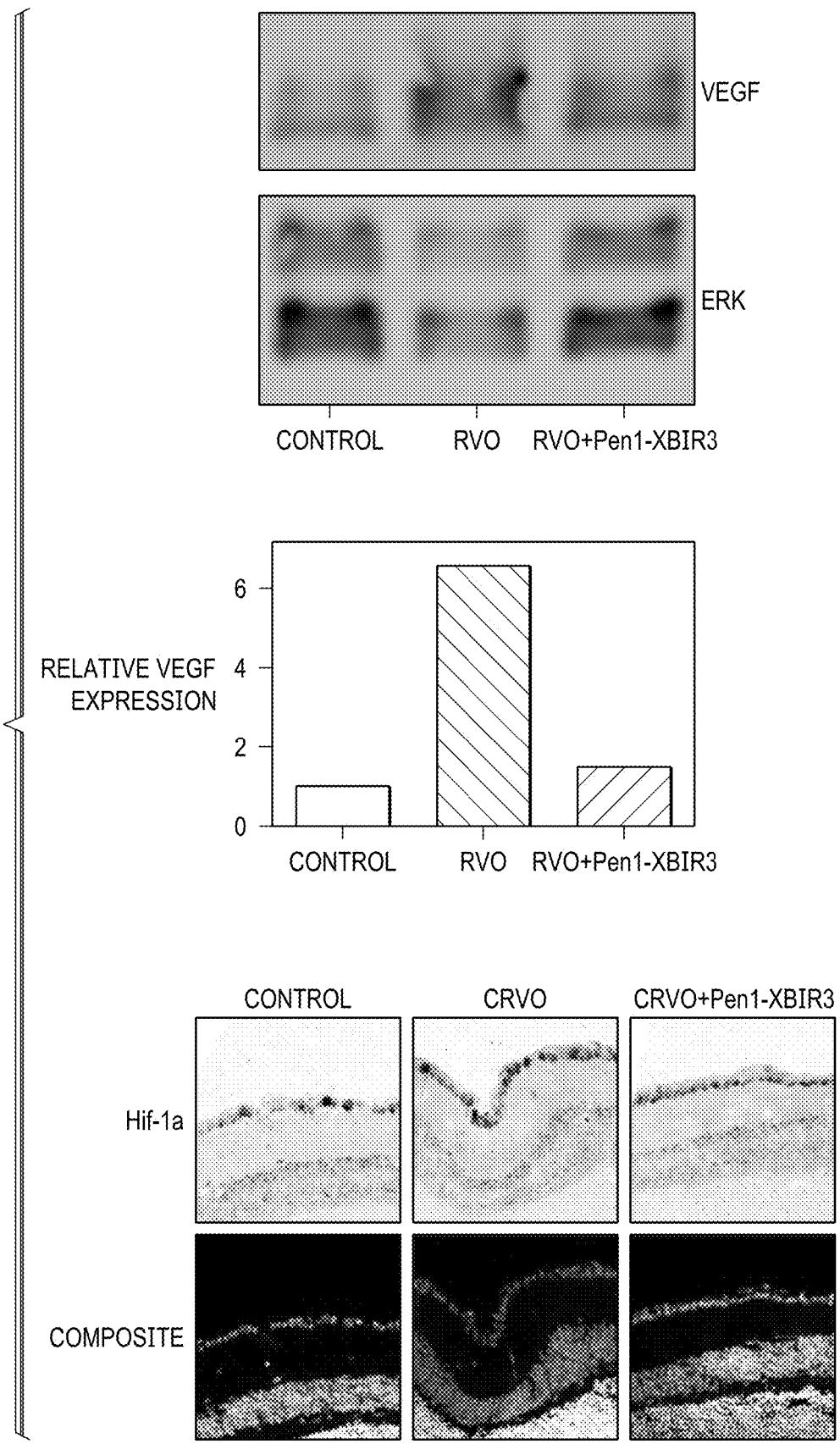
FIG. 14 is a blot showing the effects of RVO or RVO and Penl-XBIR3 on VEGF and ERK (top left), a graph showing the effects of RVO or RVO and Penl-XBIR3 on VEGF expression (bottom left), and a series of photomicrographs showing the effects of RVO or RVO and Penl-XBIR3 on HIF-1a expression in the retina.

Treatment with Penl-XBIR3 after RVO abrogated the increase in VEGF and HIF-1a. Retinas were harvested at 4 h post-RVO and analyzed by western blot for VEGF expression (FIG. 14, left) and by immunohistochemistry for HIF-1a expression (FIG. 14, right).

The present disclosure is not to be limited in scope by the specific embodiments described herein. Indeed, various modifications of the disclosure in addition to those described herein will become apparent to those skilled in the art from the foregoing description and the accompanying figures. Such modifications are to fall within the scope of the appended claims. Patents, patent applications, publications, procedures, and the like are cited throughout this application, the disclosures of which are incorporated herein by reference in their entireties.

The invention claimed is:

1. A method for treating retinal vein occlusion (RVO) in a patient in need thereof, wherein the method comprises administering to an eye having a retina of the patient an amount of an eye drop comprising a conjugate comprising an X-linked inhibitor of apoptosis (XIAP)-baculoviral IAP repeat 3 (BIR3) domain (XBIR3) and a cell-penetrating peptide, wherein the XBIR3 comprises the sequence MGSSHHHHHHSSGLVPRGSHMSTNTCLPRNPSMADYEARIFTFGTWIYSVNK EQLARAGFYTDWALGEGDKVKCFHCGGGLRPSEDPWEQHARWYPGCRYLL EQRGQEYINNIHLTHS (SEQ ID NO: 11) MGSSHHHHHHSSGLVPRGSHMSTNTLPRNPSMADYEARIFTFGTWIYSVNKE QLARAGFYTDWALGEGDKVKCFHCGGGLRPSEDPWEQHARWYPGCRYLLE QRGQEYINNIHLTHS (SEQ ID NO: 12), and wherein the amount of eye drop is effective to deliver the conjugate to the retina and treat the RVO.

2. The method of claim 1, wherein the cell-penetrating peptide is selected from the group consisting of Penetratin1, transportan, pIS1, Tat(48-60), pVEC, a model amphipathic peptide (MAP), and a membrane translocating sequence (MTS).

3. The method of claim 1, wherein the cell-penetrating peptide is Penetratin1, and wherein the conjugate comprises XBIR3 and Penetratin1 (Pen1-XBIR3).

4. The method of claim 3, wherein the Pen1-XBIR3 is present in the eye drop in a concentration of 0.1 µM to 1,000 µM.

5. The method of claim 1, wherein the amount of the eye drop effective to deliver the conjugate to the retina treats RVO by decreasing edema in the retina of the patient, as detected by optical coherence tomography (OCT).

6. The method of claim 1, wherein the amount of the eye drop effective to deliver the conjugate to the retina treats RVO by decreasing retinal detachment of the retina of the patient.

7. The method of claim 1, wherein the amount of the eye drop effective to deliver the conjugate to the retina treats RVO by decreasing clot formation in the retina of the patient.

8. The method of claim 1, wherein the eye drop is administered to the patient in a single dose.

9. The method of claim 1, wherein the eye drop is administered to the patient in multiple doses.

10. The method of claim 1, wherein the XBIR3 comprises the sequence

```
                                          (SEQ ID NO. 11)
MGSSHHHHHHSSGLVPRGSHMSTNTCLPRNPSMADYEARIF

TFGTWIYSVNKEQLARAGFYTDWALGEGDKVKCFHCGGGL

RPSEDPWEQHARWYPGCRYLLEQRGQEYINNIHLTHS.
```

11. The method of claim 1, wherein the XBIR3 comprises the sequence

```
                                          (SEQ ID NO. 12)
MGSSHHHHHHSSGLVPRGSHMSTNTLPRNPSMADYEARIF

TFGTWIYSVNKEQLARAGFYTDWALGEGDKVKCFHCGGGL

RPSEDPWEQHARWYPGCRYLLEQRGQEYINNIHLTHS.
```

12. The method of claim 1, wherein the XBIR3 is directly linked by a single covalent bond to the amino or carboxy terminus of the cell penetrating peptide.

13. The method of claim 1, wherein the XBIR3 is operably linked to the cell penetrating peptide via a chemical linker.

14. The method of claim 13, wherein the chemical linker comprises a substituted alkyl or a substituted cycloalkyl.

15. The method of claim 13, wherein the chemical linker comprises 1-30 nonhydrogen atoms selected from the group consisting of C, N, O, S and P.

16. The method of claim 15, wherein the chemical linker comprises less than 20 nonhydrogen atoms.

17. The method of claim 15, wherein the chemical linker comprises single, double, triple or aromatic carbon-carbon bonds, carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, or nitrogen-platinum bonds.

18. The method of claim 15, wherein the chemical linker comprises ether, thioether, urea, thiourea, amine, ester, carboxamide, sulfonamide, hydrazide bonds, or aromatic or heteroaromatic bonds.

19. The method of claim 15, wherein the chemical linker comprises a combination of single carbon-carbon bonds and carboxamide, sulfonamide or thioether bonds.

* * * * *

SEQUENCE LISTING

<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Glu Ile Asp
1

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(NPys)

<400> SEQUENCE: 2

Cys Arg Gln Ile Lys Ile Trp Phe Gln Asn Arg Arg Met Lys Trp Lys
1               5                   10                  15

Lys

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Leu Arg Arg Leu Leu Arg Arg Leu Leu Arg Arg Leu Arg Arg
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Val Gly Arg Arg Arg Arg Arg Arg Arg Arg Arg
1               5                   10

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu

```
            20                  25

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Val Ile Arg Val Trp Phe Gln Asn Lys Arg Cys Lys Asp Lys Lys
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Lys Lys Arg Arg Gln Arg Arg Arg Pro Pro Gln
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Ile Ile Leu Arg Arg Arg Ile Arg Lys Gln Ala His Ala His
1               5                   10                  15

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ser Ser His His His His His His Ser Ser Gly Leu Val Pro
1               5                   10                  15

Arg Gly Ser His Met Ser Thr Asn Thr Cys Leu Pro Arg Asn Pro Ser
            20                  25                  30

Met Ala Asp Tyr Glu Ala Arg Ile Phe Thr Phe Gly Thr Trp Ile Tyr
        35                  40                  45

Ser Val Asn Lys Glu Gln Leu Ala Arg Ala Gly Phe Tyr Thr Asp Trp
    50                  55                  60

Ala Leu Gly Glu Gly Asp Lys Val Lys Cys Phe His Cys Gly Gly Gly
65                  70                  75                  80

Leu Arg Pro Ser Glu Asp Pro Trp Glu Gln His Ala Arg Trp Tyr Pro
                85                  90                  95

Gly Cys Arg Tyr Leu Leu Glu Gln Arg Gly Gln Glu Tyr Ile Asn Asn
            100                 105                 110

Ile His Leu Thr His Ser
        115

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Ser Ser His His His His His His Ser Ser Gly Leu Val Pro
1               5                   10                  15

Arg Gly Ser His Met Ser Thr Asn Thr Leu Pro Arg Asn Pro Ser Met
            20                  25                  30

Ala Asp Tyr Glu Ala Arg Ile Phe Thr Phe Gly Thr Trp Ile Tyr Ser
        35                  40                  45

Val Asn Lys Glu Gln Leu Ala Arg Ala Gly Phe Tyr Thr Asp Trp Ala
    50                  55                  60

Leu Gly Glu Gly Asp Lys Val Lys Cys Phe His Cys Gly Gly Gly Leu
65                  70                  75                  80

Arg Pro Ser Glu Asp Pro Trp Glu Gln His Ala Arg Trp Tyr Pro Gly
                85                  90                  95

Cys Arg Tyr Leu Leu Glu Gln Arg Gly Gln Glu Tyr Ile Asn Asn Ile
            100                 105                 110

His Leu Thr His Ser
        115
```